United States Patent [19]

Balis et al.

[11] 4,317,877

[45] Mar. 2, 1982

[54] PROCESS FOR DETECTING THE PRESENCE OF MALIGNANT AND PRE-MALIGNANT CELLS IN HUMANS

[75] Inventors: M. Earl Balis, New York; Paul J. Higgins, East Meadow; Josephine S. Salser, Yonkers, all of N.Y.

[73] Assignee: Sloan Kettering Institute, New York, N.Y.

[21] Appl. No.: 156,827

[22] Filed: Jun. 5, 1980

[51] Int. Cl.$^3$ ............................................. G01N 33/54
[52] U.S. Cl. ............................................. 435/7; 424/8; 424/12; 435/4; 435/15
[58] Field of Search ............... 23/230 B; 424/8, 12; 435/4, 7, 174, 240, 15

[56] References Cited

U.S. PATENT DOCUMENTS 3,663,684 5/1972 Freedman et al. ...................... 424/8
3,974,269 8/1976 Maley ........................................ 435/7

OTHER PUBLICATIONS

Salser, *Cancer Research*, 36, 1976, pp. 3495-3498.
Taylor, *J. Biol. Chem.*, 247, 1972, 1930-1935.
Salser et al., *Nature* 260, 1976, pp. 261-263.
Chemical Abstracts 90:127518p "Specific Immunoserums," Matsuda et al. 1978.
Ibsen, *Biochim. Biophys. Acta*, 560, 1979, pp. 243-280.
Rees, *Methods of Cancer Research* 18, 1979 pp. 99-133.

*Primary Examiner*—Peter A. Hruskoci
*Attorney, Agent, or Firm*—Sprung, Felfe, Horn, Lynch & Kramer

[57] ABSTRACT

Malignant and pre-malignant cells in humans are detected by contacting an antibody to oncofoetal deoxythymidine kinase with human cells and detecting the presence of cells containing oncofoetal deoxythymidine kinase antigen bound to the antibody.

8 Claims, No Drawings

PROCESS FOR DETECTING THE PRESENCE OF MALIGNANT AND PRE-MALIGNANT CELLS IN HUMANS

The invention described herein was made in the course of work under a grant or award from the Department of Health, Education and Welfare.

BACKGROUND

This invention relates to a process for detecting the presence of malignant and pre-malignant cells in humans which utilizes an antibody to oncofoetal deoxythymidine kinase (TK).

The expression of oncodevelopmental by transformed cells antigens is well-documented (Ibsen et al, Biochim. Biophys. Acta, 560, 243–280 (1979); Rees et al, Methods Can. Res., 18, 99–133 (1979) and may well be a characteristic feature of many malignancies. The pyrimidine nucleoside recycling enzyme closely associated with proliferation, TK, is particularly interesting in this regard since quantitative and/or qualitative changes in TK activity invariably accompany neoplastic transformation. Progressively increasing levels of TK activity and shifts toward enzyme variants with foetal-like characteristics were present in preneoplastic and neoplastic intestinal lesions induced in rats by 1,2-dimethylhydrazine (Salser et al, Cancer Res., 36, 3495–3498 (1976); Ball, et al, Cancer Res., 36, 2686–2689 (1976)). There were also increases in the levels of the more thermolabile foetal-like TK variant(s) in the surface and the crypt of the colonic mucosa from these animals, i.e., surface vs crypt=6:1, reminiscent of the expansion of the proliferative zone to the upper two-thirds of the colon seen in carcinogen-treated mice and in patients with predilection to or prior history of colon cancer (Maskens et al, J. Nat'l. Cancer Inst., 58, 1221–1224 (1977); Deschner, Z. Krebsforsch., 91, 205–216 (1978). These data suggest that during carcinogenesis TK variant(s), qualitatively distinguishable from normal TK, begin to appear in the premalignant intestines.

In man, oncofoetal TK's have been identified (a) in several different types of cancer on the basis of electrophoretic mobilities and various biochemical parameters similar to those of foetal liver enzyme (Taylor et al, J. Biol. Chem., 247, 1930–1935 (1972); Stafford et al, Biochim. Biophys. Acta, 277, 439–442 (1972)) and (b) in colonic flat mucosa (but not in colonic crypt), several colorectal tumors and a variety of other unrelated solid tumors by using antisera produced against 2100-fold purified colonic mucosal TK to demonstrate the antigenic cross-reactivities between term-placental TK and cytosolic TK's from the above mentioned tissues (Salser et al, Nature, 260, 261–263 (1976)).

SUMMARY

The present invention provides a process for detecting the presence of malignant and pre-malignant cells of humans which comprises:

(1) contacting an antibody to oncofoetal deoxythymidine kinase with human cells; and (2) detecting the presence of cells containing oncofoetal deoxythymidine kinase antigen bound to said antibody. The antibody can be in an antiserum and can be contacted (incubated) with human cells grown in culture, human cell smears and human tissue sections. The cell-bound antibody can be detected by indirect immunofluoresence and by coupled immuno peroxidase assay. The antiserum can be prepared against placental or tumor deoxythymidine kinase.

DESCRIPTION

The present invention in one embodiment, uses an antiserum prepared against an oncodevelopmental enzyme, deoxythymidine kinase (TK), purified from human term placenta that can discriminate between normal and various malignant human cells. An indirect immunofluorescence technique is used with primary cells in culture, cervical cell smears, malignant effusion cell smears and both cryostat and formalin-fixed paraffin-embedded tissue sections. The positive cytoplasmic fluorescence of primary tumor cells in culture exhibit a perinuclear concentration; normal cells in explant cultures do not stain. In tissue sections, malignant cells within the tumors show a heterogeneous positive cytoplasmic fluorescence whereas adjacent normal cells do not. Leukaemic leucocytes and both normal and mitogen-stimulated peripheral lymphocytes do not show any reactivity to this antiserum.

To identify the TK variants and to delineate the specific TK-associated antigenic relationship between normal and malignant tissues, antisera are produced in rabbits against 4000-fold purified TK from normal colonic mucosa (pooled autopsy specimens) and 3400-fold purified TK from term-placentae. The purification procedure is as previously described (Salser et al, Nature, 260, 261–263 (1976)). The smaller molecular weight component initially resolved by gel filtration serves as the antigen. This particular placental TK, like its colonic counterpart, is comprised of a major TK variant (M. Wt., about 85,000 daltons, determined by sedimentation in a linear glycerol gradient and by gel filtration) and at least three other minor TK variants (revealed by PAGE analysis). The electrophoretically identical variants from the two sources, however, are not antigenically identical. This lack of complete identity between the two TK preparations is also borne out by the differences in the precipitin patterns (Balis et al, in "Biological Markers of Neoplasia: Basic and Applied Aspects" (edited by Ruddon, R. W.), 517–534 (Elsevier North Holland, Inc., New York, (1978)) and in the inhibition of TK activity when identical antigens are assayed with the antisera produced against these two enzymes (Table 1). The lack of complete neutralization by these antisera of their respective homologous enzymes is not unexpected since only the small molecular weight component is used as antigen. The more effective inhibition of tumor and colonic surface cells by anti-placental TK when compared to its colonic counterpart reaffirms the antigenic relatedness between these tissues reported previously (Salser et al, Cancer Res., 36, 3495–3498 (1976); Ball et al Cancer Res., 36, 2686–2689 (1976) and Salser et al, Nature, 260, 261–263 (1976). The positive cytoplasmic fluorescence obtained with anti-placental TK, but not with anti-colonic TK, when assayed in indirect immunofluorescence tests against established human tumor cell lines in culture (Table 1) can be used to differentiate malignant and pre-malignant cells from normal cells according to the invention.

Explants of human tissues are examined (Table 2) to demonstrate that anti-placental TK can discriminate between normal and malignant cells. Cells derived from some of these explants exhibit positive cytoplasmic fluorescence with a perinuclear concentration. An examination of cryostat and of formalin-fixed paraffin-embedded tissue sections (Table 3) confirms the finding with the explant cultures (Table 2). Thirteen out of 16 solid tumors of diverse origins exhibit positive cytoplasmic fluorescence, e.g., in an infiltrating squamous cell carcinoma of the epiglottis, numerous malignant cells show a markedly heterogeneous granular positive cytoplasmic fluorescence. Except for term-placentae, normal cells do not react with anti-placental TK whether they are located among other normal cells in a tissue or are adjacent to the malignant cells in a tumor. The absence of staining in cell preparations of leucophoresed leukaemic leucocytes and both normal and phytohemagglutinin-stimulated peripheral lymphocytes is consistent with earlier neutralization and immunodiffusion studies (Salser et al, Nature, 260, 261–263 (1976). Cervical and malignant effusion cell smears illustrate the feasibility of using such specimens in screening routines.

The following examples are intended to further illustrate the present invention without limiting same in any manner.

TABLE 1

Comparison of anti-colonic TK and anti-placental TK

| Neutralization* | Anti-colonic | Anti-placental |
|---|---|---|
| Normal colon | | |
| Total mucosa | 68 | 35 |
| Surface (flat mucosa) | 38 | 59 |
| Crypt | 64 | 30 |
| Term-placentae | 25 | 64 |
| Tumors | | |
| Colonic, rectal, gastric, ovarian and breast | 18–35 | 34–57 |
| Indirect Immunofluorescent test+ | negative | postive cytoplasmic fluorescence |

*Values are the percent inhibition of TK activity. Dilutions (1:10) of preimmune and sera of rabbit immunized with colonic TK (4000-fold purified) and of rabbit immunized with placental TK (3400-fold purified) are preincubated overnight at 4° with equal volumes (0.2 ml, containing 250–300 μg protein) of dialyzed preparations of TK's partially purified by two successive ammonium sulfate precipitations from the cytosol fraction of the tissue extracts. Three aliquots of the resultant supernatant solutions are removed for TK assay as previously described (Salser et al, Cancer Res., 33, 1889–1897 (1973); Cancer, 34, 889–895 (1974).

+Established human colon carcinoma and breast carcinoma cell lines are grown on glass coverslips using Eagle's Minimum Essential Medium supplemented with 10–20% fetal calf serum. Culture conditions employed have been described (Higgins et al, Rurop. J. Cancer, 15, 423–431 (1979). The growth media is aspirated from the cultures, the cells washed twice in phosphate-buffered saline (PBS), pH 7.4 and fixed in 100% methanol for 30 min at room temperature and these fixed cell preparations stored at −20°. Rabbit anti-placental TK is diluted 1:40–1:50 in foetal calf serum (or in PBS when tissue sections are processed) and used as the primary antiserum which is layered onto the rehydrated specimens (with PBS) and incubated for 1 hr at 22° in a humid chamber. Controls are preimmune serum or anti-placental TK absorbed with total placental cytosol fraction or placental TK preparations of varying degrees of purification. Washing of the cells and tissue sections for treatment with secondary fluorescein isothiocyanate-conjugated goat anti-rabbit IgG (Miles Laboratory) and subsequent fluorescence microscopy are previously described (Higgins et al, Europ. J. Cancer, 15, 423–431 (1979)).

TABLE 2

Immunofluorescent reactivity of methanol-fixed explant cultures of human tissues.

| Explant | Individual samples | Reactivity to antiplacental TK |
|---|---|---|
| Normal colon | 1 | − |
| Adenomatous polyps | 3 | + |
| Normal mammary tissue | 3 | − |
| Mammary carcinoma | | |
| Epithelioid | 3 | + |
|  | 1 | − |
| Fibroblasts | 3 | + |

Explant cultures are established from human tissues by seeding minced tissue fragments onto 60 mm petri dish cultures containing coverslips and 5 ml of foetal calf serum-supplemented growth medium according to a method described for the establishment of a mouse hepatoma cell line (Higgins, et al, Europ. J. Cancer, 15, 423–431 (1979). After 2–4 weeks of culture, the coverslips are removed and the adherent cells washed in PBS prior to fixation in 100% methanol for 30 min at room temperature. These fixed cell preparations are stored at −20° C. and are rehydrated with PBS for immunofluorescence testing as described in Table 1.

TABLE 3

Reactivity of anti-placental TK in tissue preparation.

| Tissue | Number of positive/Total |
|---|---|
| Tissue sections* | |
| Normal | |
| Colon | 0/6 |
| Salivary gland | 0/2 |
| Thymus | 0/2 |
| Term placentae | 2/2 |
| Tumor | |
| Colon adenoma | 2/2 |
| Colon adenocarcinoma | 5/6 |
| Gastric adenocarcinoma | 2/2 |
| Small intestinal tumor | 1/1 |
| Squamous carcinoma of the head and neck | 2/2 |
| Lung epidermoid carcinoma | 1/1 |
| Uterine choriocarcinoma | 0/1 |
| Auxillary melanoma | 0/1 |
| Cell smears+ | |
| Cervical cells | |
| Normal | 0/3 |
| Abnormal | 14/46 |
| Peripheral lymphocytes | |
| Normal control | 0/5 |
| phytohemagglutinin-stimulated | 0/2 |
| Leukaemic (CLL and AML) | 0/6 |
| Malignant effusions, e.g., ascitic fluids and pleural fluids | 4/4 |

*Routine 4–5 μ sections of normal and malignant human tissues are prepared by cryostat sectioning of unfixed specimens or by microtome sectioning of 100% methanol or 10% formalin-fixed paraffin-embedded tissues. Cryostat sectioned specimens are fixed in 100% methanol for 30 min at room temperature, immediately after cutting. Prior to use in the indirect immunofluorescence test (cf. Table 1), paraffin-embedded are cleared in xylene and taken through graded dilutions of ethanol.

+Cervical cell smears are samples taken for routine PAP tests. Cells from malignant effusions were collected by centrifugation and washed with PBS. Normal lymphocytes are examined either as the total buffy coat or after purification with Ficoll-Paque; leukaemic leucocytes from leucophoresis samples are also purified with Ficoll-Paque. These cell preparations are resuspended in Eagle's Minimal Essential Medium supplemented with 10% foetal calf serum and slides are prepared like standard blood smears.

The present invention can be used to diagnose human cancers other than leukemia by detecting the presence of malignant and pre-malignant cells as described above. The oncofoetal deoxythymidine kinase antigen described herein can also be used to produce monoclonal antibodies for example as described by Barnstable et al, Cell, 14, 9–20 (1978).

What is claimed is:

1. Process for detecting the presence of malignant and pre-malignant cells in humans which comprises:
   (i) incubating an antibody to placental or tumor deoxythymidine kinase with human cells; and
   (ii) detecting the presence of cells containing placental or tumor deoxythymidine kinase antigen bound to said antibody.

2. Process of claim 1 wherein the antibody is incubated in an antiserum.

3. Process of claim 1 wherein the antibody is incubated with human cells grown in culture.

4. Process of claim 1 wherein the antibody is incubated with a human cell smear.

5. Process of claim 1 wherein the antibody is incubated with a human tissue section.

6. Process of claim 1 wherein the antibody bound cells are detected by indirect immunofluorescense or by coupled immuno peroxidase assay.

7. Process of claim 1 wherein the antibody is made against placental deoxythymidine kinase.

8. Process of claim 1 wherein the antibody is made against tumor deoxythymidine kinase.

* * * * *